(12) United States Patent
Ji et al.

(10) Patent No.: US 10,112,896 B2
(45) Date of Patent: Oct. 30, 2018

(54) METHOD FOR SYNTHESIZING DISSYMMETRIC SULFOETHER

(71) Applicant: SOOCHOW UNIVERSITY, Suzhou (CN)

(72) Inventors: Shunjun Ji, Suzhou (CN); Xueqiang Chu, Suzhou (CN); Xiaoping Xu, Suzhou (CN); Wenbin Cao, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 15/537,400

(22) PCT Filed: Aug. 16, 2016

(86) PCT No.: PCT/CN2016/095469
§ 371 (c)(1),
(2) Date: Jun. 16, 2017

(87) PCT Pub. No.: WO2017/215110
PCT Pub. Date: Dec. 21, 2017

(65) Prior Publication Data
US 2018/0201576 A1 Jul. 19, 2018

(30) Foreign Application Priority Data

Jun. 15, 2016 (CN) .......................... 2016 1 0423506

(51) Int. Cl.
| | | |
|---|---|---|
| C07C 321/18 | (2006.01) | |
| C07C 321/20 | (2006.01) | |
| C07C 319/14 | (2006.01) | |
| C07C 319/28 | (2006.01) | |
| C07F 11/00 | (2006.01) | |
| C07B 45/06 | (2006.01) | |
| C07C 321/12 | (2006.01) | |

(52) U.S. Cl.
CPC ............ *C07C 321/18* (2013.01); *C07B 45/06* (2013.01); *C07C 319/14* (2013.01); *C07C 319/28* (2013.01); *C07C 321/12* (2013.01); *C07C 321/20* (2013.01); *C07F 11/005* (2013.01); *C07C 2527/12* (2013.01)

(58) Field of Classification Search
CPC ... C07C 321/18; C07C 319/14; C07C 321/20; C07C 319/28; C07C 2527/08; C07C 253/30; C07F 11/005
See application file for complete search history.

(56) References Cited

FOREIGN PATENT DOCUMENTS

| CN | 101239936 A | 8/2008 |
|---|---|---|
| CN | 103787802 A | 5/2014 |
| WO | 2015/011206 A1 | 1/2015 |

OTHER PUBLICATIONS

Qiao et al., Direct Cross-Coupling Access to Diverse Aromatic Sulfide: Palladium-Catalyzed Double C-S Bond construction Using Na2S2O3 as a Sulfurating Reagent; Org. Lett. 2014, 16, 1212-1215.
Tabarelli et al., Direct Synthesis of Allylic Thioethers Under Greener Conditions: A Solventand Catalyst-Free Approach; Synthetic Communications, 44: 3441-3449, 2014.
Li et al., Stereoselective synthesis of naturally occurring unsaturated amide alkaloids by a modified Ramberg-Bäcklund reaction; Can. J. Chem. 82: 622-630 (2004).
Edwards et al., Allyl sulphides in olefin metathesis: catalyst considerations and traceless promotion of ring-closing metathesis, Chem. Commun., 2015, 51, 515 (published on Nov. 20, 2014).
Chu et al., One-Pot Synthesis of Allylic Sulfones, Ketosulfones, and Triflyl Allylic Alcohols from Domino Reactions of Allylic Alcohols with Sulfinic Acid under Metal-Free Conditions, Chem. Eur. J. 2015, 21, 11359-11368 (published on Jun. 11, 2015).
Yang et al., Sulfuration of the C(sp2)—H bond of enaminones:a protocol for the synthesis of thioether using elemental sulfur as a sulfurating reagent, Org. Biomol. Chem. 2016, 14, 2993 (published on Feb. 4, 2016).
Gu et al., The involvement of the trisulfur radical anion in electron-catalyzed sulfur insertion reactions: facile synthesis of benzothiazine derivatives under transition metal-free conditions, Chem. Sci. 2016, 7, 4067 (published on Mar. 11, 2016).
Maeno et al., Trifluoromethyl Sulfoxides from Allylic Alcohols and Electrophilic SCF3 Donor by [2,3]-Sigmatropic Rearrangement, Org. Lett. 2015, 17, 1990-1993 (Apr. 1, 2015).
Office action dated Jun. 19, 2017 issued in corresponding Chinese patent application No. CN 201610423506.2.

*Primary Examiner* — Rosalynd A Keys

(74) *Attorney, Agent, or Firm* — SZDC Law P.C.

(57) ABSTRACT

A method for synthesizing dissymmetric sulfoether includes the following step: a) under the condition of tetrabutylammonium halide catalysis, compounds having a structure of formula (I), compounds having a structure of formula (II) and salts having sulfur and oxygen are reacted in a solvent to give dissymmetric sulfoether having a structure of formula (III).

9 Claims, No Drawings

METHOD FOR SYNTHESIZING DISSYMMETRIC SULFOETHER

The present application is a national stage application of PCT/CN2016/095469, filed on Aug. 16, 2016, which claims priority to Chinese patent application No. 201610423506.2, titled "Method for Synthesizing Dissymmetric Sulfoether", filed with the Chinese State Intellectual Property Office on Jun. 15, 2016, the entire contents of which are incorporated herein by reference.

FIELD

The present application relates to the field of organic chemistry, and more particularly to a synthetic method of dissymmetric sulfoether.

BACKGROUND

Dissymmetric sulfoether is a kind of important sulfur-containing compounds. It is not only widely found in natural products, pharmaceutically active molecules, but also acts as advanced materials and metal ligands, or as important organic synthesis intermediates.

Dissymmetric sulfoether compounds have a wide range of applications in biomedicine, for example:

Methionine is one of the essential amino acids in the human body, and it participates in protein synthesis. Because it can not be generated by the body itself, it must be obtained from the outside. Lack of methionine will lead to inhibition of protein synthesis in vivo, causing damage to the body. At present, methionine is usually synthesized by the coupling reaction of halide and thiol and its related derivatives under the catalysis of transition metal.

Cilastatin is a thiamycin antibiotic with carbapenem ring, which is a commercially available antimicrobial agent prepared by semi-synthesis of thiamycin from culture medium of *S. cattleya*. Cilastatin is used for sepsis caused by sensitive organism, infective endocarditis, osteomyelitis, arthritis, skin and soft tissue infections. At present, Cilastatin is synthesized by direct addition of thiol and its related derivatives to unsaturated compounds under the condition with transition metal or no metal.

Cinanserin can be used to treat psychiatric disorders. At present, Cinanserin is usually synthesized by addition of thiol and its related derivatives to alkynes under the condition of transition metal catalyst.

It can be seen that thiol compounds, which are highly toxic, malodorous, sensitive and perishable, are inevitably used in the reaction process of the current method for synthesizing dissymmetric sulfoether in addition to the need for expensive metal catalyst and harsh reaction conditions (anhydrous, anaerobic, etc.). These shortcomings seriously restrict the practical use of the method. Therefore, the development of novel synthetic methods for dissymmetric sulfoether compounds has been a hot research field in organic chemistry and pharmaceutical chemistry.

SUMMARY

In view of the above, it is an object of the present application to provide a method for synthesizing dissymmetric sulfoether. The method provided by the present application has a mild reaction condition and is environment-friendly.

A method for synthesizing dissymmetric sulfoether is provided in the present application, comprising the following step:

a) under the condition of tetrabutylammonium halide catalysis, the compounds having a structure of formula (I), the compounds having a structure of formula (II) and salts having sulfur and oxygen are reacted in a solvent to give dissymmetric sulfoether having a structure of formula (III);

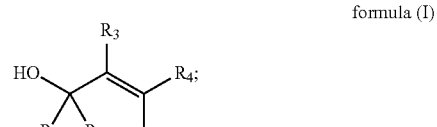

formula (I)

formula (II)

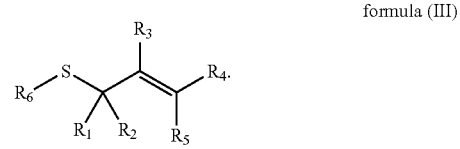

formula (III)

Wherein, $R_1$ is selected from phenyl, substituted phenyl, naphthyl, substituted naphthyl, thienyl or substituted thienyl; $R_2$ is selected from hydrogen, phenyl, substituted phenyl, naphthyl, substituted naphthyl, thienyl or substituted thienyl; or $R_1$, $R_2$ form fluorene ring or thioxanthone ring with the C to which it is attached;

$R_3$ is selected from hydrogen or alkyl;

$R_4$ is selected from hydrogen, phenyl, substituted phenyl, naphthyl, substituted naphthyl, thienyl or substituted thienyl; $R_5$ is selected from hydrogen; or $R_4$, $R_5$ form fluorene ring or thioxanthone ring with the C to which it is attached;

$R_6$ is selected from C1~C30 alkyl, cyano-substituted C1~C20 alkyl, cyano-substituted C1~C20 benzyl, C1~C5 alkyl-substituted benzyl, halogen-substituted benzyl, fluorenyl and any one of the structural substituents represented in formulas (a-1)~(a-9):

(a-1)

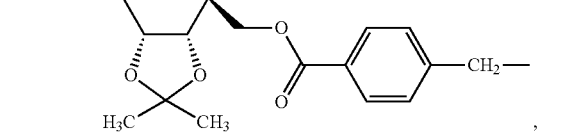

(a-2)

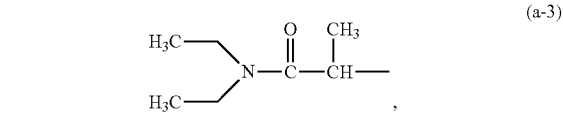

(a-3)

-continued

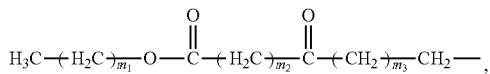
(a-4)

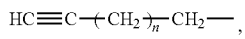
(a-5)

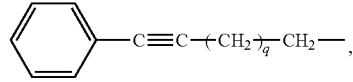
(a-6)

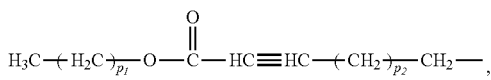
(a-7)

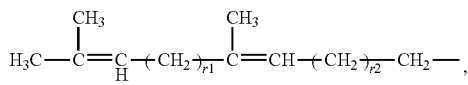
(a-8)

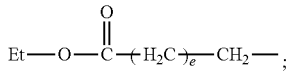
(a-9)

in formulas (a-4)~(a-9), $m_1$, $m_2$, $m_3$, n, q, $p_1$, $p_2$, $r_1$, $r_2$ and e are integers from 0 to 5, respectively;

X is selected from Cl, Br or I;

said salts having sulfur and oxygen include sodium thiosulfate and/or sodium sulfite.

Preferably, $R_1$ is selected from phenyl, C1~C5 alkyl-substituted phenyl, C1~C5 alkoxy-substituted phenyl, halogen-substituted phenyl, naphthyl, C1~C5 alkyl-substituted naphthyl, C1~C5 alkoxy-substituted naphthyl, halogen-substituted naphthyl, thienyl, C1~C5 alkyl-substituted thienyl, C1~C5 alkoxy-substituted thienyl or halogen-substituted thienyl.

Preferably, $R_2$ is selected from hydrogen, phenyl, C1~C5 alkyl-substituted phenyl, C1~C5 alkoxy-substituted phenyl, halogen-substituted phenyl, naphthyl, C1~C5 alkyl-substituted naphthyl, C1~C5 alkoxy-substituted naphthyl, halogen-substituted naphthyl, thienyl, C1~C5 alkyl-substituted thienyl, C1~C5 alkoxy-substituted thienyl or halogen-substituted thienyl.

Preferably, $R_3$ is selected from hydrogen and C1~C5 alkyl.

Preferably, $R_4$ is selected from hydrogen, phenyl, C1~C5 alkyl-substituted phenyl, halogen-substituted phenyl, naphthyl, C1~C5 alkyl-substituted naphthyl, halogen-substituted naphthyl, thienyl, C1~C5 alkyl-substituted thienyl or halogen-substituted thienyl.

Preferably, said structural compound of formula (I) is 1,1-diphenylpropyl-2-enyl-1-ol, 1,1-bis (4-fluorophenyl) prop-2-enyl-1-ol, 1,1-bis (4-chlorophenyl) prop-2-enyl-1-ol, 1,1-bis (4-bromophenyl) prop-2-enyl-1-ol, 1,1-bis (4-methylphenyl) prop-2-enyl-1-ol, 1,1-bis (4-methoxyphenyl) prop-2-enyl-1-ol, 1-phenyl-1-p-methylphenyl-2-enyl-1-ol, 1-(3,4-dimethylphenyl)-1-phenylprop-2-enyl-1-ol, 1-phenyl-1-p-bromophenyl-2-enyl-1-ol, 1-phenyl-1-o-fluorophenylprop-2-enyl-1-ol, 1-(naphthalen-2-yl)-1-phenylprop-2-enyl-1-ol, 2-methyl-1,1-diphenylprop-2-enyl-1-ol, 9-ethenyl-9H-fluorenyl-9-ol, 9-ethenyl-9H-thioxanthen-9-ol, 1-phenylprop-2-enyl-1-ol, (E)-1,3-diphenylprop-2-enyl-1-ol, (E)-1,3-bis (4-fluorophenyl) prop-2-enyl-1-ol, (E)-1,3-bis (4-chlorophenyl) prop-2-enyl-1-ol, (E)-1,3-bis (4-bromophenyl) prop-2-enyl-1-ol, (E)-1,3-bis (naphthalen-2-yl) prop-2-enyl-1-ol, (E)-1,3-bis (thiophen-2-yl) prop-2-enyl-1-ol or (E)-2-methyl-1,3-diphenylprop-2-enyl-1-ol.

Preferably, said structural compound of formula (II) is p-cyanobenzyl chloride, m-cyanobenzyl chloride, p-trifluoromethylbenzyl chloride, o-bromobenzyl chloride, p-methylbenzyl bromide, 9-bromofluorene, (4-(chloromethyl) phenyl) (1H-indol-1-yl) methanone, ((3aR, 5S, 5aS, 8aS, 8bR)-2,2,7,7-tetramethyltetrahydroxy-3aH-bis [1,3] dioxo [4,5-b: 4',5'-d] pyran-5-yl) methyl 4-(chloromethyl) phenyl ester, (3-chloropropyl-1-ynyl) benzene, iodine n-decane, 4-chlorobutyronitrile or ethyl 4-bromobutyrate.

Preferably, molar ratio of structural compounds of formula (I): structural compounds of formula (II): salts having sulfur and oxygen is 1:(1.5~3):(2~4).

Preferably, temperature of said reaction is 20~90° C.

Preferably, time of said reaction is 3~8 h.

Preferably, in step a), after the completion of reaction of structural compounds of formula (I), structural compounds of formula (II) and salts having sulfur and oxygen, extraction, drying and column chromatography are performed successively to give dissymmetric sulfoether having a structure represented in formula (III).

Preferably, said solvent is water.

Compared with the prior art, the present application provides a method for synthesizing dissymmetric sulfoether. The method provided in the present application comprises the following step a) under the condition of tetrabutylammonium halide catalysis, the compounds having a structure of formula (I), the compounds having a structure of formula (II) and salts having sulfur and oxygen are reacted in a solvent to give dissymmetric sulfoether having a structure of formula (III).

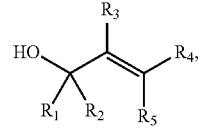
formula (I)

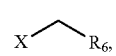
formula (II)

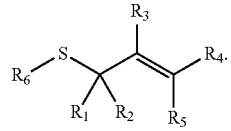
formula (III)

Wherein $R_1$ is selected from phenyl, substituted phenyl, naphthyl, substituted naphthyl, thienyl or substituted thienyl; $R_2$ is selected from hydrogen, phenyl, substituted phenyl, naphthyl, substituted naphthyl, thienyl or substituted thienyl; or $R_1$, $R_2$ form fluorene ring or thioxanthone ring with the C to which it is attached; $R_3$ is selected from hydrogen or alkyl; $R_4$ is selected from hydrogen, phenyl, substituted phenyl, naphthyl, substituted naphthyl, thienyl or substituted thienyl; $R_5$ is selected from hydrogen; or $R_4$, $R_5$ form fluorene ring or thioxanthone ring with the C to which it is attached; $R_6$ is selected from alkyl or substituted alkyl; X is selected from Cl, Br or I; said salts having sulfur and oxygen include sodium thiosulfate and/or sodium sulfite. In the method provided in the present application, substituted aryl allyl alcohol compounds, substituted alkyl halides and salts having sulfur and oxygen are used as the reaction raw materials and tetrabutylammonium halide as a catalyst, using one-pot method to prepare dissymmetric sulfoether. In this method, the raw materials are cheap and easy to obtain, the catalytic conditions are simple, mild and without the participation of transition metals, and the yield is relatively high. In addition, in the preferred embodiment of the present application, the reaction is carried out in the aqueous phase, meeting the green chemistry requirements. The results of experiments show that the method provided by the present application can synthesize a series of dissymmetric sulfoether with potential biological and pharmacological activity, and the highest product yield is more than 91%.

DETAILED DESCRIPTION OF THE EMBODIMENTS

The technical solution in the embodiments of the present application will be described below clearly and completely. Obviously, the described embodiments are merely part of the present invention, and not all embodiments. All other embodiments obtained by those of ordinary skill in the art based on embodiments in the present application without making creative work are within the scope of the present invention.

A method for synthesizing dissymmetric sulfoether is provided in the present application, comprising the following step:

a) under the condition of tetrabutylammonium halide catalysis, the compounds having a structure of formula (I), the compounds having a structure of formula (II) and salts having sulfur and oxygen are reacted in a solvent to give dissymmetric sulfoether having a structure of formula (III);

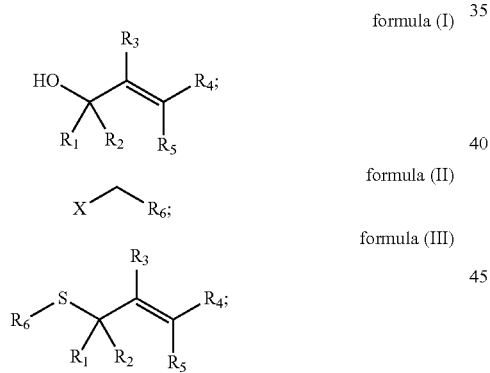

formula (I)

formula (II)

formula (III)

wherein, $R_1$ is selected from phenyl, substituted phenyl, naphthyl, substituted naphthyl, thienyl or substituted thienyl; $R_2$ is selected from hydrogen, phenyl, substituted phenyl, naphthyl, substituted naphthyl, thienyl or substituted thienyl; or $R_1$, $R_2$ form a fluorene ring or thioxanthone ring with the C to which it is attached;

$R_3$ is selected from hydrogen or alkyl;

$R_4$ is selected from hydrogen, phenyl, substituted phenyl, naphthyl, substituted naphthyl, thienyl or substituted thienyl; $R_5$ is selected from hydrogen; or $R_4$, $R_5$ form a fluorene ring or thioxanthone ring with the C to which it is attached;

$R_6$ is selected from C1~C30 alkyl, cyano-substituted C1~C20 alkyl, cyano-substituted C1~C20 benzyl, C1~C5 alkyl-substituted benzyl, halogen-substituted benzyl, fluorenyl and any one of the structural substituents represented in formulas (a-1)~(a-9):

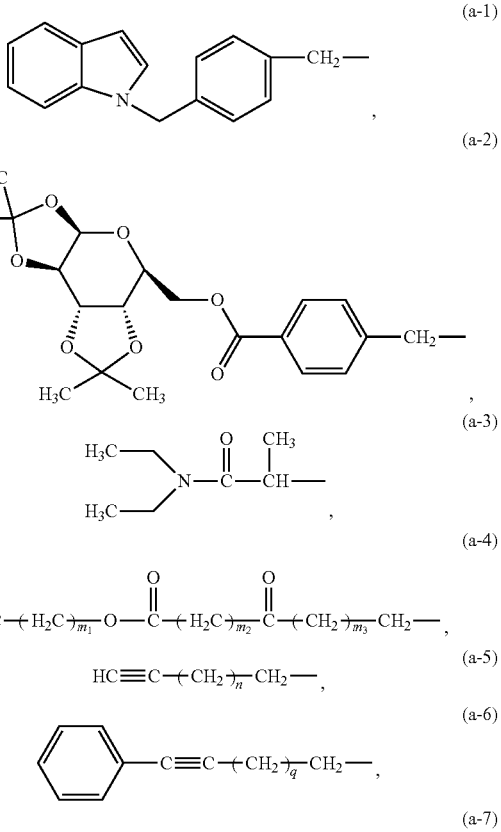

In formulas (a-4)~(a-9), $m_1$, $m_2$, $m_3$, n, q, $p_1$, $p_2$, $r_1$, $r_2$ and e are integers from 0 to 5, respectively;

X is selected from Cl, Br or I;

said salts having sulfur and oxygen include sodium thiosulfate and/or sodium sulfite.

In the synthetic method provided by the present application, the compounds having a structure of formula (I), the compounds having a structure of formula (II) and salts having sulfur and oxygen are reacted in a solvent with tetrabutylammonium halide catalysis. Wherein, the structure of said structural compound in formula (I) is as below:

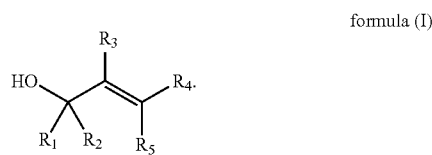

formula (I)

In formula (I), $R_1$ is selected from phenyl, substituted phenyl, naphthyl, substituted naphthyl, thienyl or substituted thienyl; preferably, it is selected from phenyl, C1~C5 alkyl-substituted phenyl, C1~C5 alkoxy-substituted phenyl, halogen-substituted phenyl, naphthyl, C1~C5 alkyl-substituted naphthyl, C1~C5 alkoxy-substituted naphthyl, halogen-substituted naphthyl, thienyl, C1~C5 alkyl-substituted thienyl, C1~C5 alkoxy-substituted thienyl or halogen-substituted thienyl; more preferably, it is selected from phenyl, fluorophenyl, chlorophenyl, bromophenyl, methylphenyl, dimethylphenyl, methoxyphenyl, naphthyl or thienyl; most preferably, it is selected from phenyl, 4-fluorophenyl, o-fluorophenyl, 4-chlorophenyl, 4-bromophenyl, p-bromophenyl, 4-methylphenyl, p-methylphenyl, 3,4-dimethylphenyl, 4-methoxyphenyl, naphthalen-2-yl or thiophen-2-yl; $R_2$ is selected from hydrogen, phenyl, substituted phenyl, naphthyl, substituted naphthyl, thienyl or substituted thienyl; preferably, it is selected from hydrogen, phenyl, C1~C5 alkyl-substituted phenyl, C1~C5 alkoxy-substituted phenyl, halogen-substituted phenyl, naphthyl, C1~C5 alkyl-substituted naphthyl, C1~C5 alkoxy-substituted naphthyl, halogen-substituted naphthyl, thienyl, C1~C5 alkyl-substituted thienyl, C1~C5 alkoxy-substituted thienyl or halogen-substituted thienyl; more preferably, it is selected from hydrogen, phenyl, fluorophenyl, chlorophenyl, bromophenyl, methylphenyl, dimethylphenyl, methoxyphenyl, naphthyl or thienyl; most preferably, it is selected from hydrogen, phenyl, 4-fluorophenyl, o-fluorophenyl, 4-chlorophenyl, 4-bromophenyl, p-bromophenyl, 4-methylphenyl, p-methylphenyl, 3,4-dimethylphenyl, 4-methoxyphenyl, naphthalen-2-yl or thiophen-2-yl. Or $R_1$, $R_2$ form a fluorene ring or thioxanthone ring with the C to which it is attached.

In formula (I), $R_3$ is selected from hydrogen or alkyl, preferably from hydrogen, C1~C5 alkyl, more preferably from hydrogen, methyl or ethyl.

In formula (I), $R_4$ is selected from hydrogen, phenyl, substituted phenyl, naphthyl, substituted naphthyl, thienyl or substituted thienyl; preferably, it is selected from hydrogen, phenyl, C1~C5 alkyl-substituted phenyl, halogen-substituted phenyl, naphthyl, C1~C5 alkyl-substituted naphthyl, halogen-substituted naphthyl, halogen-substituted thienyl, C1~C5 alkyl-substituted thienyl or halogen-substituted thienyl; more preferably, it is selected from hydrogen, phenyl, fluorophenyl, chlorophenyl, bromophenyl, naphthyl or thienyl; most preferably, it is selected from hydrogen, phenyl, 4-fluorophenyl, 4-chlorophenyl, 4-bromophenyl or naphthalen-2-yl or thiophen-2-yl. $R_5$ is selected from hydrogen. Or $R_4$, $R_5$ form a fluorene ring or thioxanthone ring with the C to which it is attached.

In one embodiment provided in the present application, said structural compound of formula (I) is 1,1-diphenylpropyl-2-enyl-1-ol (1), 1,1-bis (4-fluorophenyl) prop-2-enyl-1-ol (2), 1,1-bis (4-chlorophenyl) prop-2-enyl-1-ol (3), 1,1-bis (4-bromophenyl) prop-2-enyl-1-ol (4), 1,1-bis (4-methylphenyl) prop-2-enyl-1-ol (5), 1,1-bis (4-methoxyphenyl) prop-2-enyl-1-ol (6), 1-phenyl-1-p-methylphenyl-2-enyl-1-ol, 1-(3,4-dimethylphenyl)-1-phenylprop-2-enyl-1-ol (8), 1-phenyl-1-p-bromophenyl-2-enyl-1-ol (9), 1-phenyl-1-o-fluorophenylprop-2-enyl-1-ol (10), 1-(naphthalen-2-yl)-1-phenylprop-2-enyl-1-ol (11), 2-methyl-1,1-diphenylprop-2-enyl-1-ol (12), 9-ethenyl-9H-fluorenyl-9-ol, 9-ethenyl-9H-thioxanthen-9-ol, 1-phenylprop-2-enyl-1-ol (15), (E)-1,3-diphenylprop-2-enyl-1-ol (16), (E)-1,3-bis (4-fluorophenyl) prop-2-enyl-1-ol (17), (E)-1,3-bis (4-chlorophenyl) prop-2-enyl-1-ol (18), (E)-1,3-bis (4-bromophenyl) prop-2-enyl-1-ol (19), (E)-1,3-bis (naphthalen-2-yl) prop-2-enyl-1-ol (20), (E)-1,3-bis (thiophen-2-yl) prop-2-enyl-1-ol (21) or (E)-2-methyl-1,3-diphenylprop-2-enyl-1-ol (22). In the present application, the specific structures of the structural compound (I) having a structures of formulas (1)~(22) are as below:

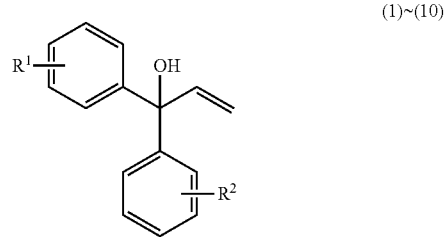
(1)~(10)

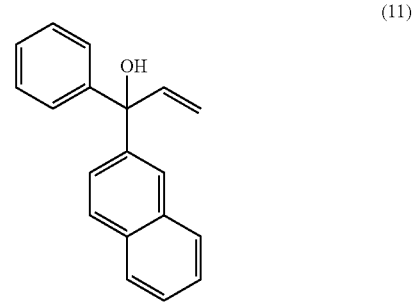
(11)

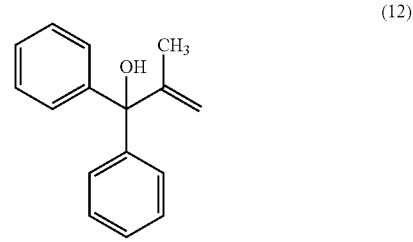
(12)

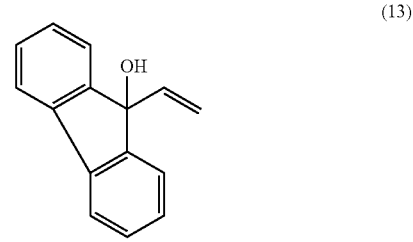
(13)

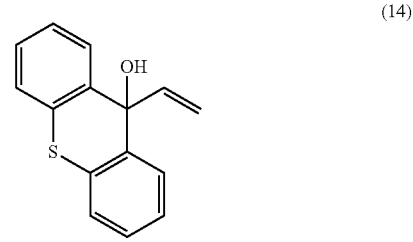
(14)

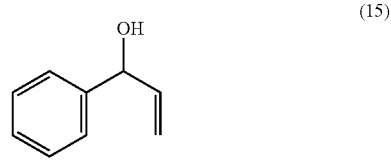
(15)

(16)~(19)

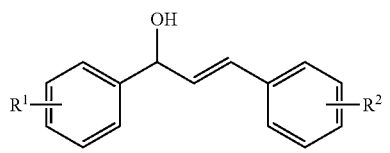

(20)

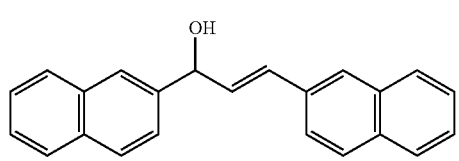

(21)

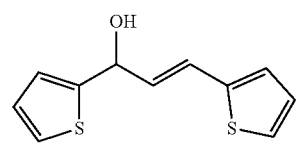

(22)

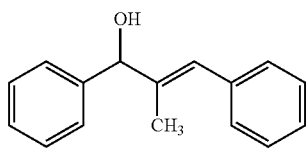

In formulas (1)~(10), for the name of corresponding numbering compound, $R^1$ can be selected from hydrogen, fluorine, chlorine, bromine, methyl, methoxy or dimethyl; $R^2$ can be selected from hydrogen, fluorine, chlorine, bromine, methyl, methoxy or dimethyl. In formulas (16)~(19), for the name of corresponding numbering compound, $R^1$ can be selected from hydrogen, fluorine, chlorine or bromine; $R^2$ can be selected from hydrogen, fluorine, chlorine or bromine.

In the present application, structure of said structural compounds of formula (II) is as below:

$$X\diagup\!\!\!\diagdown R_6 \qquad \text{formula (II)}$$

In formula (II), $R_6$ is selected from C1~C30 alkyl, cyano-substituted C1~C20 alkyl, benzyl, C1~C5 alkyl-substituted benzyl, halogen-substituted benzyl, fluorenyl or any of the structural substituents of formulas (a-1)~(a-9):

(a-1)

(a-2)

(a-3)

(a-4)

(a-5)

(a-6)

(a-7)

(a-8)

(a-9)

In formulas (a-4)~(a-9), $m_1$, $m_2$, $m_3$, n, q, $p_1$, $p_2$, $r_1$, $r_2$ and e are integers from 0 to 5, respectively.

In one embodiment provided in the present application, said structural compound of formula (II) is p-cyanobenzyl chloride (23), m-cyanobenzyl chloride (24), p-trifluoromethylbenzyl chloride (25), o-bromobenzyl chloride (26), p-methylbenzyl bromide (27), 9-bromofluorene (28), (4-(chloromethyl) phenyl) (1H-1-indolyl) methanone (29), ((3aR, 5S, 5aS, 8aS, 8bR)-2,2,7,7-tetramethyltetrahydroxy-3aH-bis [1,3] dioxo [4,5-b: 4',5'-d]5-pyranyl) methyl 4-(chloromethyl) phenyl ester (30), (3-chloropropyl-1-ynyl) benzene (35), iodine iodobutane (38), iodine n-decane (39), 4-chlorobutyronitrile (40) or ethyl 4-bromobutyrate (41). In the present application, structures of said structural compounds of formula (II) having structures of formulas (23)~(41) are as below:

(23)~(27)

(28)

-continued

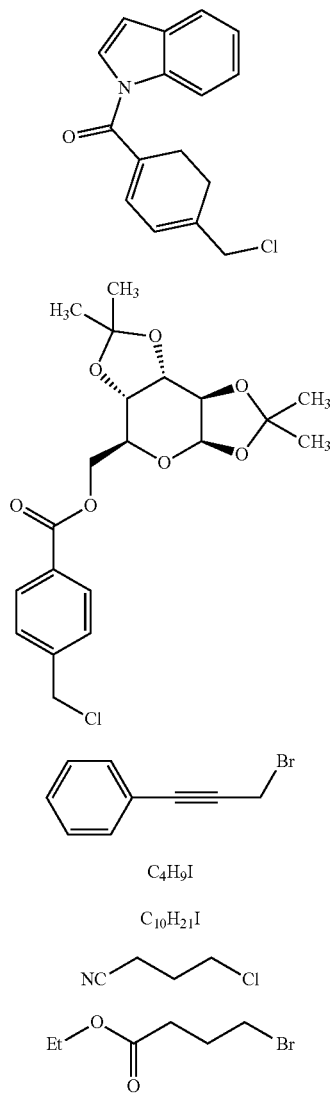

(29)

(30)

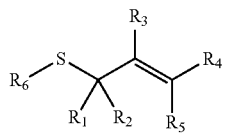

(35)

C$_4$H$_9$I (38)

C$_{10}$H$_{21}$I (39)

(40)

(41)

In formulas (23)~(27), for the name of corresponding numbering compound, R can be selected from cyano, trifluoromethyl, bromo or methyl; X can be selected from chlorine or bromine.

In the present application, said salts having sulfur and oxygen include sodium thiosulfate and/or sodium sulfite, preferably sodium thiosulfate; said solvent is preferably water. Said molar ratio of structural compound of formula (I): structural compound of formula (II): salt having sulfur and oxygen is preferably 1:(1.5~3):(2~4), more preferably 1:(1.5~2.4):(2~4), even more preferably 1:(1.5~2):(2~2.4), most preferably 1:2:2.4. Said molar ratio of tetrabutylammonium halide to structural compound of formula (I) is preferably (0.01~1):1, more preferably (0.1~0.5):1, most preferably 0.2:1. Said usage ratio of solvent to structural compound of formula (I) is preferably (0.1~10)mL:(0.1~0.5)mmol, more preferably (0.5~2)mL:(0.1~0.5)mmol, most preferably 1 mL:0.3 mmol.

In the present application, during the reaction procedure of structural compound of formula (I), structural compound of formula (II), salt having sulfur and oxygen, said reaction is preferably carried out under confined conditions; temperature of said reaction is preferably 20~90° C., more preferably 25~80° C., even more preferably 70~80° C., most preferably 80° C.; time of said reaction is preferably 3~8 h, more preferably 5~6 h. After the completion of reaction, reaction solution is obtained and said reaction solution is subjected to extraction, drying and column chromatography, respectively. Herein, extractant used in said extraction is preferably ethyl acetate; desiccant used in said drying is preferably anhydrous sodium sulfate; stationary phase used in said column chromatography is preferably 300~400 mesh silica gel powder; mobile phase of said column chromatography is preferably ethyl acetate and petroleum ether. After the completion of column chromatography, dissymmetric sulfoether having a structure of formula (III) are obtained:

$$\underset{R_1\ R_2\ \ R_5}{R_6\diagdown S\diagdown \underset{}{\overset{R_3}{\diagup}}\diagup R_4} \qquad \text{formula (III)}$$

In formula (III), the selection ranges of $R_1$~$R_6$ are consistent with those of formulas (I) and (II), and are not described again here.

In the method provided in the present application, substituted aryl allyl alcohol compounds, substituted alkyl halides and salts having sulfur and oxygen are used as the reaction raw materials and tetrabutylammonium halide as a catalyst, using one-pot method to prepare dissymmetric sulfoether. In this method, the raw materials are cheap and easy to obtain, the catalytic conditions are simple, mild and without the participation of transition metals, and the yield is relatively high. In addition, in the preferred embodiment of the present application, the reaction is carried out in the aqueous phase, meeting the green chemistry requirements. The results of experiments show that the method provided by the present application can synthesize a series of dissymmetric sulfoether with potential biological and pharmacological activity, and the highest product yield is more than 91%.

For a clearer understanding, the present application is described in detail through the following examples.

Example 1

Synthesis of 4-((3,3-diarylablylthio) methyl) benzonitrile 0.3 mmol 1,1-diphenylprop-2-enyl-1-ol (0.0631 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0778 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.49~7.42 (m, 2H), 7.38~7.33 (m, 3H), 7.29~7.25 (m, 3H), 7.22~7.18 (m, 2H), 7.18~7.13 (m, 4H), 6.08 (t, J=7.8 Hz, 1H), 3.63 (s, 2H), 3.18 (d, J=7.8 Hz, 2H) ppm.

According to the characterization data, it can be seen that the reaction product was pure product of 4-((3,3-diaryl allylthio) methyl) benzonitrile (purity>95%); the product yield was calculated and the result was 76%.

Example 2

Synthesis of 4-((3,3-bis (4-fluorophenyl) allylthio) methyl) benzonitrile 0.3 mmol 1,1-bis (4-fluorophenyl) prop-2-enyl-1-ol (0.0739 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0932 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.51 (d, J=8.3 Hz, 2H), 7.24 (d, J=8.2 Hz, 2H), 7.16~7.09 (m, 4H), 7.09~7.03 (m, 2H), 7.00~6.94 (m, 2H), 6.01 (t, J=7.8 Hz, 1H), 3.65 (s, 2H), 3.14 (d, J=7.9 Hz, 2H) ppm.

According to the characterization data, it can be seen that the reaction product was pure product of 4-((3,3-bis (4-fluorophenyl) allylthio) methyl) benzonitrile (purity>95%); the product yield was calculated and the result was 82%.

Example 3

Synthesis of 4-((3,3-bis (4-chlorophenyl) allylthio) methyl) benzonitrile 0.3 mmol 1,1-bis (4-chlorophenyl) prop-2-enyl-1-ol (0.0837 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0865 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.56~7.52 (m, 2H), 7.38~7.35 (m, 2H), 7.29~7.24 (m, 4H), 7.13~7.08 (m, 4H), 6.08 (t, J=7.9 Hz, 1H), 3.66 (s, 2H), 3.16 (d, J=7.9 Hz, 2H) ppm.

According to the characterization data, it can be seen that the reaction product was pure product of 4-((3,3-bis (4-chlorophenyl) allylthio) methyl) benzonitrile (purity>95%); the product yield was calculated and the result was 80%.

Example 4

Synthesis of 4-((3,3-bis (4-bromophenyl) allylthio) methyl) benzonitrile 0.3 mmol 1,1-bis (4-bromophenyl) prop-2-enyl-1-ol (0.1104 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.1361 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.54~7.47 (m, 4H), 7.42~7.38 (m, 2H), 7.21 (d, J=8.3 Hz, 2H), 7.05~6.99 (m, 4H), 6.07 (t, J=7.9 Hz, 1H), 3.64 (s, 2H), 3.12 (d, J=7.9 Hz, 2H) ppm.

According to the characterization data, it can be seen that the reaction product was pure product of 4-((3,3-bis (4-bromophenyl) allylthio) methyl) benzonitrile (purity>95%); the product yield was calculated and the result was 71%.

Example 5

Synthesis of 4-((3,3-p-tolyl allylthio) methyl) benzonitrile 0.3 mmol 1,1-bis (4-methylphenyl) prop-2-enyl-1-ol (0.0715 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0898 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.45 (d, J=8.3 Hz, 2H), 7.16 (dd, J=7.8, 5.7 Hz, 4H), 7.09 (s, 4H), 7.03 (d, J=8.0 Hz, 2H), 6.00 (t, J=7.8 Hz, 1H), 3.62 (s, 2H), 3.18 (d, J=7.8 Hz, 2H), 2.41 (s, 3H), 2.33 (s, 3H) ppm.

According to the characterization data, it can be seen that the reaction product was pure product of 4-((3,3-p-tolyl allylthio) methyl) benzonitrile (purity>95%); the product yield was calculated and the result was 76%.

Example 6

Synthesis of 4-((3,3-p-methoxyphenyl allylthio) methyl) benzonitrile 0.3 mmol 1,1-bis (4-methoxyphenyl) prop-2-enyl-1-ol (0.0811 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0970 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.50~7.44 (m, 2H), 7.19 (d, J=8.3 Hz, 2H), 7.16~7.12 (m, 2H), 7.09~7.04 (m, 2H), 6.90~6.85 (m, 2H), 6.83~6.79 (m, 2H), 5.93 (t, J=7.8 Hz, 1H), 3.85 (s, 3H), 3.80 (s, 3H), 3.63 (s, 2H), 3.18 (d, J=7.8 Hz, 2H) ppm.

According to the characterization data, it can be seen that the reaction product was pure product of 4-((3,3-p-methoxyphenyl allylthio) methyl) benzonitrile (purity>95%); the product yield was calculated and the result was 60%.

Example 7

Synthesis of 4-((3-phenyl-3-p-tolylthio) methyl) benzonitrile 0.3 mmol 1-phenyl-1-p-methylphenyl-2-en-1-ol (0.0673 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0745 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.45 (d, J=8.1 Hz, 2H), 7.34 (dd, J=4.1, 2.4 Hz, 1H), 7.27 (d, J=7.2 Hz, 1H), 7.22~7.19 (m, 1H), 7.18~7.13 (m, 3.0 Hz, 4H), 7.09 (s, 2H), 7.03 (d, J=8.0 Hz, 1H), 6.09~6.00 (m, 1H), 3.62 (d, J=2.1 Hz, 2H), 3.18 (dd, J=9.1, 7.9 Hz, 2H), 2.41 (s, 1.5H), 2.33 (s, 1.5H) ppm.

According to the characterization data, it can be seen that the reaction product was pure product of 4-((3-phenyl-3-p-tolylthio) methyl) benzonitrile (purity>95%); the product yield was calculated and the result was 67%.

Example 8

Synthesis of 4-((3-(3,4-dimethylphenyl)-3-phenylallylthio) methyl) benzonitrile 0.3 mm ol 1-(3,4-dimethylphenyl)-1-phenylprop-2-enyl-1-ol (0.0715 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0886 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.47~7.42 (m, 2H), 7.36~7.32 (m, 1.8H), 7.28~7.26 (m, 1.2H), 7.24~7.20 (m, 1H), 7.18~7.09 (m, 3.2H), 7.04 (d, J=7.8 Hz, 0.7H), 6.98 (s, 0.5H), 6.93~6.86 (m, 1.5H), 6.02 (t, J=7.8 Hz, 1H), 3.62 (d, J=3.3 Hz, 2H), 3.18 (dd, J=12.1, 7.8 Hz, 2H), 2.31 (s, 1.5H), 2.24 (d, J=4.3 Hz, 3H), 2.22 (s, 1.5H) ppm.

According to the characterization data, it can be seen that the reaction product was pure product of 4-((3-(3,4-dimethylphenyl)-3-phenylallylthio) methyl) benzonitrile (purity>95%); the product yield was calculated and the result was 79%.

Example 9

Synthesis of 4-((3-phenyl-3-p-bromophenylthio) methyl) benzonitrile 0.3 mmol 1-phenyl-1-p-bromophenyl-2-en-1-ol (0.0868 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0840 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.53~7.44 (m, 3H), 7.41~7.35 (m, 3H), 7.29~7.26 (m, 1H), 7.22 (d, J=8.3 Hz, 1H), 7.18~7.11 (m, 3H), 7.08~7.01 (m, 2H), 6.11~6.03 (m, 1H), 3.63 (d, J=10.7 Hz, 2H), 3.15 (dd, J=7.9, 3.6 Hz, 2H) ppm.

According to the characterization data, it can be seen that the reaction product was pure product of 4-((3-phenyl-3-p-bromophenylthio) methyl) benzonitrile (purity>95%); the product yield was calculated and the result was 67%.

Example 10

Synthesis of 4-((3-phenyl-3-o-fluorophenylthio) methyl) benzonitrile 0.3 mmol 1-phenyl-1-p-bromophenyl-2-en-1-ol (0.0685 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0669 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.48 (d, J=8.2 Hz, 1H), 7.42 (d, J=8.2 Hz, 1H), 7.38-7.26 (m, 4H), 7.23 (d, J=5.0 Hz, 1H), 7.21-7.17 (m, 1H), 7.16-7.11 (m, 3H), 7.10-7.01 (m, 2H), 6.22 (t, J=7.7 Hz, 0.45H), 6.02 (t, J=7.6 Hz, 0.55H), 3.65 (s, 2H), 3.24 (d, J=7.7 Hz, 1.1H), 3.10 (d, J=7.7 Hz, 0.9H) ppm.

According to the characterization data, it can be seen that the reaction product was pure product of 4-((3-phenyl-3-o-fluorophenylthio) methyl) benzonitrile (purity>95%); the product yield was calculated and the result was 62%.

Example 11

Synthesis of 4-((3-(naphthalen-2-yl)-3-phenylallylthio) methyl) benzonitrile 0.3 mmol 1-(naphthalen-2-yl)-1-phenylprop-2-enyl-1-ol (0.0781 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0678 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.93~7.79 (m, 3H), 7.69 (d, J=8.5 Hz, 0.5H), 7.50~7.40 (m, 3.5H), 7.40~7.33 (m, 2.5H), 7.32~7.24 (m, 4.5H), 7.13 (d, J=8.3 Hz, 1.2H), 6.99 (d, J=8.3 Hz, 0.8H), 6.42 (t, J=7.7 Hz, 0.45H), 5.96 (t, J=7.8 Hz, 0.55H), 3.71 (s, 1.1H), 3.59~3.48 (m, 0.9H), 3.40 (d, J=7.8 Hz, 1.1H), 2.94 (d, J=7.7 Hz, 0.9H) ppm.

According to the characterization data, it can be seen that the reaction product was pure product of 4-((3-(naphthalen-2-yl)-3-phenylallylthio) methyl) benzonitrile (purity>95%); the product yield was calculated and the result was 76%.

Example 12

Synthesis of 4-((2-methyl-3,3-diphenylallylthio) methyl) benzonitrile 0.3 mmol 2-methyl-1,1-diphenylprop-2-enyl-1-ol (0.0673 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0806 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.49~7.44 (m, 2H), 7.30~7.22 (m, 6H), 7.16 (d, J=8.3 Hz, 2H), 7.13~7.09 (m, 3H), 7.08 (s, 1H), 3.60 (s, 2H), 3.24 (s, 2H), 1.89 (s, 3H) ppm.

According to the characterization data, it can be seen that the reaction product was pure product of 4-((2-methyl-3,3-diphenylallylthio) methyl) benzonitrile (purity>95%); the product yield was calculated and the result was 74%.

Example 13

Synthesis of 4-((2-(9H-fluoren-9-ylidene) ethylthio) methyl) benzonitrile 0.3 mmol 9-alkenyl-9H-fluorenyl-9-ol (0.0625 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0593 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.73 (d, J=7.5 Hz, 1H), 7.69 (d, J=7.5 Hz, 1H), 7.60 (d, J=7.5 Hz, 1H), 7.51 (d, J=7.7 Hz, 1H), 7.45 (d, J=8.2 Hz, 2H), 7.40~7.34 (m, 2H), 7.32~7.27 (m, 3H), 7.22~7.16 (m, 1H), 6.61 (t, J=8.2 Hz, 1H), 3.81 (d, J=8.2 Hz, 2H), 3.75 (s, 2H) ppm.

According to the characterization data, it can be seen that the reaction product was pure product of 4-((2-(9H-fluoren-9-ylidene) ethylthio) methyl) benzonitrile (purity>95%); the product yield was calculated and the result was 58%.

Example 14

Synthesis of 4-((2-(9H-thioxanthen-9-yl) ethylthio) methyl) benzonitrile 0.3 mmol 9-alkenyl-9H-thioxanthene-9-ol (0.0721 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0867 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.52~7.45 (m, 2H), 7.44~7.40 (m, 1H), 7.35~7.26 (m, 5H), 7.26~7.23 (m, 1H), 7.20~7.14 (m, 1H), 7.04 (d, J=8.3 Hz, 2H), 5.88 (t, J=7.7 Hz, 1H), 3.53 (s, 2H), 3.35 (d, J=7.7 Hz, 2H) ppm.

According to the characterization data, it can be seen that the reaction product was pure product of 4-((2-(9H-thioxanthen-9-yl) ethylthio) methyl) benzonitrile (purity>95%); the product yield was calculated and the result was 62%.

Example 15

Synthesis of 4-(cinnamylthiomethyl) benzonitrile 0.3 mmol 1-phenylprop-2-enyl-1-ol (0.0403 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0867 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.60 (d, J=8.3 Hz, 2H), 7.43 (d, J=8.3 Hz, 2H), 7.36-7.29 (m, 4H), 7.28-7.25 (m, 1H), 6.36 (d, J=15.7 Hz, 1H), 6.18-6.09 (m, 1H), 3.72 (s, 2H), 3.21 (dd, J=7.3, 0.9 Hz, 2H) ppm.

According to the characterization data, it can be seen that the reaction product was pure product of 4-(cinnamylthiomethyl) benzonitrile (purity>95%); the product yield was calculated and the result was 23%.

Example 16

Synthesis of (E)-4-((1,3-diphenylallylthio) methyl) benzonitrile 0.3 mmol (E)-1,3-diphenylprop-2-enyl-1-ol (0.0631 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0848 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.60~7.54 (m, 2H), 7.39 (s, 1H), 7.37~7.30 (m, 8H), 7.29~7.27 (m, 1H), 7.27~7.21 (m, 2H), 6.43~6.32 (m, 2H), 4.44 (d, J=7.7 Hz, 1H), 3.75~3.60 (m, 2H) ppm.

According to the characterization data, it can be seen that the reaction product was pure product of (E)-4-((1,3-diphenylallylthio) methyl) benzonitrile (purity>95%); the product yield was calculated and the result was 74%.

Example 17

Synthesis of (E)-4-((1,3-bis (4-fluorophenyl) allylthio) methyl) benzonitrile 0.3 mmol (E)-1,3-bis (4-fluorophenyl) prop-2-enyl-1-ol (0.0739 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0993 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.60 (d, J=8.3 Hz, 2H), 7.38 (d, J=8.2 Hz, 2H), 7.35~7.29 (m, 4H), 7.07~6.97 (m, 4H), 6.35 (d, J=15.7 Hz, 1H), 6.26~6.19 (m, 1H), 4.41 (d, J=8.4 Hz, 1H), 3.74~3.61 (m, 2H) ppm.

According to the characterization data, it can be seen that the reaction product was pure product of (E)-4-((1,3-bis (4-fluorophenyl) allylthio) methyl) benzonitrile (purity>95%); the product yield was calculated and the result was 91%.

Example 18

Synthesis of (E)-4-((1,3-bis (4-chlorophenyl) allylthio) methyl) benzonitrile 0.3 mmol (E)-1,3-bis (4-chlorophenyl) prop-2-enyl-1-ol (0.0837 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0887 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.60 (d, J=8.2 Hz, 2H), 7.37 (d, J=8.2 Hz, 2H), 7.34~7.25 (m, 8H), 6.41~6.21 (m, 2H), 4.39 (d, J=7.9 Hz, 1H), 3.75~3.59 (m, 2H) ppm.

According to the characterization data, it can be seen that the reaction product was pure product of (E)-4-((1,3-bis (4-chlorophenyl) allylthio) methyl) benzonitrile (purity>95%); the product yield was calculated and the result was 72%.

Example 19

Synthesis of (E)-4-((1,3-bis (4-bromophenyl) allylthio) methyl) benzonitrile 0.3 mmol (E)-1,3-bis (4-bromophenyl) prop-2-enyl-1-ol (0.1104 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.1242 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.62~7.58 (m, 2H), 7.48~7.42 (m, 4H), 7.37 (d, J=8.3 Hz, 2H), 7.24~7.18 (m, 4H), 6.35~6.25 (m, 2H), 4.37 (d, J=7.0 Hz, 1H), 3.73~3.60 (m, 2H) ppm.

According to the characterization data, it can be seen that the reaction product was pure product of (E)-4-((1,3-bis (4-bromophenyl) allylthio) methyl) benzonitrile (purity>95%); the product yield was calculated and the result was 83%.

Example 20

Synthesis of (E)-4-((1,3-bis (naphthalen-2-yl) allylthio) methyl) benzonitrile 0.3 mmol (E)-1,3-bis (naphthalen-2-yl) prop-2-enyl-1-ol (0.0931 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0566 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.89~7.76 (m, 8H), 7.70 (s, 1H), 7.60~7.54 (m, 4H), 7.51~7.42 (m, 5H), 7.39 (d, J=8.2 Hz, 2H), 6.67~6.54 (m, 2H), 4.68 (d, J=7.3 Hz, 1H), 3.79~3.63 (m, 2H) ppm.

According to the characterization data, it can be seen that the reaction product was pure product of (E)-4-((1,3-bis (naphthalen-2-yl) allylthio) methyl) benzonitrile (purity>95%); the product yield was calculated and the result was 43%.

Example 21

Synthesis of (E)-4-((1,3-bis (thiophen-2-yl) allylthio) methyl) benzonitrile 0.3 mmol (E)-1,3-bis (thiophen-2-yl) prop-2-enyl-1-ol (0.0667 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0674 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.60 (d, J=8.3 Hz, 2H), 7.42 (d, J=8.2 Hz, 2H), 7.27 (d, J=1.3 Hz, 1H), 7.19 (dd, J=4.6, 1.4 Hz, 1H), 7.01~6.94 (m, 4H), 6.56 (d, J=15.5 Hz, 1H), 6.14 (dd, J=15.5, 8.6 Hz, 1H), 4.67 (d, J=8.6 Hz, 1H), 3.82~3.70 (m, 2H) ppm.

According to the characterization data, it can be seen that the reaction product was pure product of (E)-4-((1,3-bis (thiophen-2-yl) allylthio) methyl) benzonitrile (purity>95%); the product yield was calculated and the result was 60%.

Example 22

Synthesis of (E)-4-((2-methyl-1,3-biphenylalerythio) methyl) benzonitrile 0.3 mmol (E)-2-methyl-1,3-diphenylprop-2-enyl-1-ol (0.0673 g), 0.6 mmol of cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0793 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.59 (d, J=8.2 Hz, 2H), 7.40 (d, J=8.2 Hz, 2H), 7.38~7.30 (m, 8H), 7.27~7.21 (m, 3H), 6.58 (s, 1H), 4.43 (s, 1H), 3.75~3.63 (m, 2H), 1.82 (d, J=1.1 Hz, 3H) ppm.

According to the characterization data, it can be seen that the reaction product was pure product of (E)-4-((2-methyl-1,3-biphenylalerythio) methyl) benzonitrile (purity>95%); the product yield was calculated and the result was 74%.

Example 23

Synthesis of (E)-3-((1,3-diphenylallylthio) methyl) benzonitrile 0.3 mmol (E)-1,3-diphenylprop-2-enyl-1-ol (0.0631 g), 0.6 mmol of m-cyanobenzyl chloride (0.0910 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0677 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.57~7.50 (m, 3H), 7.42~7.38 (m, 2H), 7.36~7.31 (m, 6H), 7.30~7.21 (m, 3H), 6.46~6.33 (m, 2H), 4.45 (d, J=7.7 Hz, 1H), 3.73~3.58 (m, 2H) ppm.

According to the characterization data, it can be seen that the reaction product was pure product of (E)-3-((1,3-diphenylallylthio) methyl) benzonitrile (purity>95%); the product yield was calculated and the result was 66%.

Example 24

Synthesis of (E)-(1,3-diphenylallyl) (4-(trifluoromethyl) benzyl) sulfoether 0.3 mmol (E)-1,3-diphenylprop-2-enyl-1-ol (0.0631 g), 0.6 mmol of p-trifluoromethylbenzyl chloride (0.1167 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0773 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.63 (d, J=8.0 Hz, 2H), 7.48 (d, J=8.0 Hz, 2H), 7.46~7.38 (m, 7H), 7.37~7.29 (m, 3H), 6.53~6.39 (m, 2H), 4.52 (d, J=7.6 Hz, 1H), 3.84~3.70 (m, 2H). ppm.

According to the characterization data, it can be seen that the reaction product was pure product of (E)-(1,3-diphenylallyl) (4-(trifluoromethyl) benzyl) sulfoether (purity>95%); the product yield was calculated and the result was 67%.

Example 25

Synthesis of (E)-(2-bromobenzyl) (1,3-diphenylallyl) sulfoether 0.3 mmol (E)-1,3-diphenylprop-2-enyl-1-ol (0.0631 g), 0.6 mmol of o-bromobenzyl chloride (0.1233 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0868 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=δ 7.54 (dd, J=8.0, 1.3 Hz, 1H), 7.44~7.40 (m, 2H), 7.40~7.35 (m, 3H), 7.35~7.27 (m, 5H), 7.27~7.25 (m, 1H), 7.24~7.20 (m, 1H), 7.13~7.06 (m, 1H), 6.53~6.35 (m, 2H), 4.59 (d, J=8.3 Hz, 1H), 3.87~3.73 (m, 2H) ppm.

According to the characterization data, it can be seen that the reaction product was pure product of (E)-(2-bromobenzyl) (1,3-diphenylallyl) sulfoether (purity>95%); the product yield was calculated and the result was 73%.

Example 26

Synthesis of (E)-(4-methylbenzyl) (1,3-diphenylallyl) sulfoether 0.3 mmol (E)-1,3-diphenylprop-2-enyl-1-ol (0.0631 g), 0.6 mmol of p-methylbenzyl bromide (0.1110 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0852 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.41-7.35 (m, 4H), 7.35~7.25 (m, 5H), 7.24~7.17 (m, 3H), 7.12 (d, J=7.6 Hz, 2H), 6.48-6.34 (m, 2H), 4.45 (d, J=6.8 Hz, 1H), 3.70~3.57 (m, 2H), 2.34 (s, 3H) ppm.

According to the characterization data, it can be seen that the reaction product was pure product of (E)-(4-methylbenzyl) (1,3-diphenylallyl) sulfoether (purity>95%); the product yield was calculated and the result was 86%.

Example 27

Synthesis of (E)-(1,3-diphenylallyl) (9H-fluoren-9-yl) sulfoether 0.3 mmol (E)-1,3-diphenylprop-2-enyl-1-ol (0.0631 g), 0.6 mmol of 9-bromofluorene (0.1471 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0854 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.72~7.69 (m, 1H), 7.62~7.57 (m, 2H), 7.51 (d, J=7.3 Hz, 1H), 7.38~7.33 (m, 1H), 7.31 (d, J=1.9 Hz, 1H), 7.30~7.25 (m, 5H), 7.23~7.19

(m, 1H), 6.94~6.90 (m, 2H), 6.88~6.83 (m, 2H), 6.00~5.92 (m, 1H), 5.62 (d, J=15.6 Hz, 1H), 4.93 (s, 1H), 4.17~4.10 (m, 1H) ppm.

According to the characterization data, it can be seen that the reaction product was pure product of (E)-(1,3-diphenyl-allyl) (9H-fluoren-9-yl) sulfoether (purity>95%); the product yield was calculated and the result was 72%.

Example 28

Synthesis of (E)-1-(4-((1,3-diphenylallylthio)methyl) phenyl)-1H-indole 0.3 mmol (E)-1,3-diphenylprop-2-enyl-1-ol (0.0631 g), 0.6 mmol of (4-(chloromethyl) phenyl) (1H-indol-1-yl) methanone (0.1618 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0574 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=8.40 (d, J=8.2 Hz, 1H), 7.74~7.67 (m, 2H), 7.63~7.58 (m, 1H), 7.46 (d, J=8.0 Hz, 2H), 7.42~7.35 (m, 6H), 7.34~7.26 (m, 6H), 7.26 (d, J=1.5 Hz, 1H), 6.62 (d, J=3.8 Hz, 1H), 6.52~6.34 (m, 2H), 4.51 (d, J=7.7 Hz, 1H), 3.82~3.68 (m, 2H) ppm.

According to the characterization data, it can be seen that the reaction product was pure product of (E)-1-(4-((1,3-diphenylallylthio) methyl) phenyl)-1H-indole (purity>95%); the product yield was calculated and the result was 42%.

Example 29

Synthesis of (3aR, 5S, 5aS, 8aS, 8bR)-2,2,7,7-tetramethyltetrahydroxy-3aH-bis [1,3] dioxo [4,5-b: 4',5'-d] pyran-5-yl) methyl 4-(((E)-1,3-diphenylallyl thio) methyl) phenyl ester 0.3 mmol (E)-1,3-diphenylprop-2-enyl-1-ol (0.0631 g), 0.6 mmol of (3aR, 5S, 5aS, 8aS, 8bR)-2,2,7,7-tetramethyltetrahydroxy-3aH-bis [1,3] dioxo [4,5-b: 4',5'-d] pyran-5-yl) methyl 4-(chloromethyl) phenyl ester (0.2477 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.1227 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=8.00 (d, J=8.2 Hz, 2H), 7.37 (d, J=7.9 Hz, 6H), 7.34~7.30 (m, 3H), 7.30~7.21 (m, 3H), 6.39 (d, J=7.3 Hz, 2H), 5.58 (d, J=5.0 Hz, 1H), 4.66 (dd, J=7.9, 2.6 Hz, 1H), 4.54 (dd, J=11.5, 4.9 Hz, 1H), 4.44 (dd, J=11.1, 7.3 Hz, 2H), 4.38~4.32 (m, 2H), 4.22~4.17 (m, 1H), 3.77~3.61 (m, 2H), 1.53 (s, 3H), 1.49 (s, 3H), 1.36 (s, 3H), 1.34 (s, 3H) ppm.

According to the characterization data, it can be seen that the reaction product was pure product of (3aR, 5S, 5aS, 8aS, 8bR)-2,2,7,7-tetramethyltetrahydroxy-3aH-bis [1,3] dioxo [4,5-b: 4',5'-d] pyran-5-yl) methyl 4-(((E)-1,3-diphenylallyl thio) methyl) phenyl ester (purity>95%); the product yield was calculated and the result was 68%.

Example 30

Synthesis of (E)-2-(1,3-diphenylallyl thio) acetonitrile 0.3 mmol (E)-1,3-diphenylprop-2-enyl-1-ol (0.0631 g), 0.6 mmol of chloroacetonitrile (0.0453 g), 0.72 mmol of sodium thiosulfate (0.1138 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.1130 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.54~7.49 (m, 2H), 7.49~7.43 (m, 2H), 7.36~7.30 (m, 2H), 7.29~7.24 (m, 2H), 6.58 (d, J=15.6 Hz, 1H), 6.31 (dd, J=15.6, 9.0 Hz, 1H), 4.83 (d, J=8.9 Hz, 1H), 3.31~3.06 (m, 2H) ppm.

According to the characterization data, it can be seen that the reaction product was pure product of (E)-2-(1,3-diphenylallyl thio) acetonitrile (purity>95%); the product yield was calculated and the result was 89%.

Example 31

Synthesis of (E)-4-(1,3-diphenylallylthio)-3-oxobutanoate 0.3 mmol (E)-1,3-diphenylprop-2-enyl-1-ol (0.0631 g), 0.6 mmol of 1-bromoacetoacetate (0.0453 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0901 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.43~7.38 (m, 4H), 7.37~7.28 (m, 5H), 7.25~7.21 (m, 1H), 6.56 (d, J=15.7 Hz,

1H), 6.34 (dd, J=15.7, 9.0 Hz, 1H), 4.59 (d, J=9.1 Hz, 1H), 4.21~4.14 (m, 2H), 3.61 (s, 2H), 3.44~3.27 (m, 2H), 1.26 (t, J=7.2 Hz, 3H) ppm.

According to the characterization data, it can be seen that the reaction product was pure product of (E)-4-(1,3-diphenylallylthio)-3-oxobutanoate (purity>95%); the product yield was calculated and the result was 85%.

Example 32

Synthesis of (E)-2-(1,3-diphenylallylthio)-N, N-diethylpropionamide 0.3 mmol (E)-1,3-diphenylprop-2-enyl-1-ol (0.0631 g), 0.6 mmol of 2-bromo-N, N-diethylpropionamide (0.1249 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0692 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.46~7.40 (m, 2H), 7.40~7.32 (m, 4H), 7.32~7.26 (m, 3H), 7.25~7.19 (m, 1H), 6.57~6.48 (m, 1H), 6.47~6.38 (m, 1H), 4.71 (d, J=8.4 Hz, 1H), 3.62~3.55 (m, 1H), 3.48~3.37 (m, 2H), 3.35~3.29 (m, 1H), 3.27~3.13 (m, 2H), 3.10~2.94 (m, 1H), 1.57~1.47 (m, 3H), 1.11~1.04 (m, 3H), 1.00~0.91 (m, 3H) ppm.

According to the characterization data, it can be seen that the reaction product was pure product of (E)-2-(1,3-diphenylallylthio)-N, N-diethylpropionamide (purity>95%); the product yield was calculated and the result was 65%.

Example 33

Synthesis of (E)-(1,3-diphenylallyl) (prop-2-ynyl) sulfoether 0.3 mmol (E)-1,3-diphenylprop-2-enyl-1-ol (0.0631 g), 0.6 mmol of bromopropyne (0.0714 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0714 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.48~7.43 (m, 2H), 7.41~7.35 (m, 3H), 7.34~7.25 (m, 5H), 6.59 (d, J=15.6 Hz, 1H), 6.39 (dd, J=15.6, 8.9 Hz, 1H), 4.87 (d, J=8.9 Hz, 1H), 3.24 (dd, J=16.9, 2.6 Hz, 1H), 3.09 (dd, J=16.9, 2.6 Hz, 1H), 2.30 (t, J=2.6 Hz, 1H) ppm.

According to the characterization data, it can be seen that the reaction product was pure product of (E)-(1,3-diphenylallyl) (prop-2-ynyl) sulfoether (purity>95%); the product yield was calculated and the result was 90%.

Example 34

Synthesis of (E)-(1,3-diphenylallyl) (phenylprop-2-ynyl) sulfoether 0.3 mmol (E)-1,3-diphenylprop-2-enyl-1-ol (0.0631 g), 0.6 mmol of 1-phenyl-3-chloro-1-propyne (0.0904 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0669 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.50~7.44 (m, 4H), 7.42~7.37 (m, 3H), 7.37~7.35 (m, 1H), 7.35~7.27 (m, 6H), 7.25~7.21 (m, 1H), 6.61 (d, J=15.7 Hz, 1H), 6.48~6.39 (m, 1H), 4.93 (d, J=8.8 Hz, 1H), 3.48 (d, J=16.8 Hz, 1H), 3.34 (d, J=16.8 Hz, 1H) ppm.

According to the characterization data, it can be seen that the reaction product was pure product of (E)-(1,3-diphenylallyl) (phenylprop-2-ynyl) sulfoether (purity>95%); the product yield was calculated and the result was 66%.

Example 35

Synthesis of (E)-4-((E)-1,3-diphenylallyl thio) but-2-enoic acid ethyl ester 0.3 mmol (E)-1,3-diphenylprop-2-enyl-1-ol (0.0631 g), 0.6 mmol of ethyl 4-bromocrotonate (0.1158 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0642 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.43~7.39 (m, 3H), 7.39~7.32 (m, 4H), 7.31~7.27 (m, 2H), 7.25~7.21 (m, 1H), 6.96~6.89 (m, 1H), 6.48 (d, J=15.7 Hz, 1H), 6.36 (dd, J=15.7, 8.6 Hz, 1H), 5.88-5.81 (m, 1H), 4.57 (d, J=8.6 Hz, 1H), 4.24~4.17 (m, 2H), 3.29~3.21 (m, 1H), 3.17~3.09 (m, 1H), 1.30 (t, J=7.1 Hz, 3H) ppm.

According to the characterization data, it can be seen that the reaction product was pure product of (E)-4-((E)-1,3- diphenylallyl thio) but-2-enoic acid ethyl ester (purity>95%); the product yield was calculated and the result was 63%.

Example 36

Synthesis of ((E)-3,7-dimethyloxin-2,6-dienyl) ((E)-1,3-diphenylallyl) sulfoether 0.3 mmol (E)-1,3-diphenylprop-2-enyl-1-ol (0.0631 g), 0.6 mmol of geranyl bromide (0.1303 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0801 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.43~7.40 (m, 2H), 7.39~7.36 (m, 2H), 7.35~7.26 (m, 5H), 7.24~7.20 (m, 1H), 6.50~6.36 (m, 2H), 5.31~5.24 (m, 1H), 5.14~5.07 (m, 1H), 4.60 (d, J=7.5 Hz, 1H), 3.20~3.12 (m, 1H), 3.11~3.03 (m, 1H), 2.12~2.00 (m, 4H), 1.69 (s, 3H), 1.62 (s, 3H), 1.57 (s, 3H) ppm.

According to the characterization data, it can be seen that the reaction product was pure product of ((E)-3,7-dimethyloxin-2,6-dienyl) ((E)-1,3-diphenylallyl) sulfoether (purity>95%); the product yield was calculated and the result was 74%.

Example 37

Synthesis of (E)-tert-butyl (1,3-diphenylallyl) sulfoether 0.3 mmol (E)-1,3-diphenylprop-2-enyl-1-ol (0.0631 g), 0.6 mmol of n-butane (0.1104 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0611 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.44~7.37 (m, 4H), 7.36~7.25 (m, 5H), 7.24~7.20 (m, 1H), 6.49 (d, J=15.7 Hz, 1H), 6.44~6.34 (m, 1H), 4.59 (d, J=8.4 Hz, 1H), 2.54~2.42 (m, 2H), 1.61~1.54 (m, 2H), 1.43~1.33 (m, 2H), 0.88 (t, J=7.3 Hz, 3H) ppm.

According to the characterization data, it can be seen that the reaction product was pure product of (E)-tert-butyl (1,3-diphenylallyl) sulfoether (purity>95%); the product yield was calculated and the result was 72%.

Example 38

Synthesis of (E)-decyl (1,3-diphenylallyl) sulfoether 0.3 mmol (E)-1,3-diphenylprop-2-enyl-1-ol (0.0631 g), 0.6 mmol of n-decane (0.1609 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0869 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.44~7.37 (m, 4H), 7.36~7.29 (m, 4H), 7.29~7.26 (m, 1H), 7.24~7.21 (m, 1H), 6.49 (d, J=15.7 Hz, 1H), 6.43~6.35 (m, 1H), 4.59 (d, J=8.4 Hz, 1H), 2.54~2.39 (m, 2H), 1.63~1.51 (m, 3H), 1.37~1.24 (m, 13H), 0.88 (t, J=6.8 Hz, 3H) ppm.

According to the characterization data, it can be seen that the reaction product was pure product of (E)-decyl (1,3-diphenylallyl) sulfoether (purity>95%); the product yield was calculated and the result was 79%.

Example 39

Synthesis of (E)-4-(1,3-diphenylallylthio) nitrile 0.3 mmol (E)-1,3-diphenylprop-2-enyl-1-ol (0.0631 g), 0.6 mmol of 4-chlorobutyronitrile (0.0621 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0621 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.42~7.37 (m, 4H), 7.35~7.26 (m, 5H), 7.25~7.22 (m, 1H), 6.52 (d, J=15.6 Hz, 1H), 6.42~6.34 (m, 1H), 4.60 (d, J=8.7 Hz, 1H), 2.68~2.53 (m, 2H), 2.49~2.42 (m, 2H), 1.95~1.86 (m, 2H) ppm.

According to the characterization data, it can be seen that the reaction product was pure product of (E)-4-(1,3-diphenylallylthio) nitrile (purity>95%); the product yield was calculated and the result was 71%.

Example 40

Synthesis of (E)-ethyl 4-(1,3-diphenylallyl thio) butyrate 0.3 mmol (E)-1,3-diphenylprop-2-enyl-1-ol (0.0631 g), 0.6 mmol of ethyl 4-bromobutyrate (0.1170 g), 0.72 mmol of sodium thiosulfate (0.0988 g) and 0.06 mmol of tetrabutylammonium iodide (0.0222 g) were weighed and placed in 20 mL reaction tube. 1 ml water was added to the reaction tube as a solvent, and the tube was sealed. Reaction was carried out with stirring at 80° C. for 5 hours. After completion of the reaction, the reaction solution was dried by ethyl acetate and anhydrous sodium sulfate and separated by column chromatography, successively, to yield 0.0844 g of reaction product. Conditions for column chromatography were: 300~400 mesh silica gel powder as stationary phase, ethyl acetate (A) and petroleum ether (B) as mobile phase, changing program of mobile phase (A:B) from 1:20 to 1:6.

The reaction product was characterized and result was as follows:

$^1$H NMR (400 MHz, CDCl$_3$): δ=7.44~7.39 (m, 3H), 7.38~7.35 (m, 2H), 7.34~7.30 (m, 3H), 7.29~7.26 (m, 1H), 7.24~7.21 (m, 1H), 6.50 (d, J=15.6 Hz, 1H), 6.42~6.34 (m, 1H), 4.60 (d, J=8.7 Hz, 1H), 4.13~4.06 (m, 2H), 2.60~2.45 (m, 2H), 2.44~2.37 (m, 2H), 1.99~1.85 (m, 2H), 1.22 (t, J=7.2 Hz, 3H) ppm.

According to the characterization data, it can be seen that the reaction product was pure product of (E)-ethyl 4-(1,3-diphenylallyl thio) butyrate (purity>95%); the product yield was calculated and the result was 83%.

The foregoing is only preferred embodiments of the present application. It should be noted that several improvements and modifications may be made by those ordinary skill in the art without departing from the principles of the invention, which should be regarded within the protection scope of the present invention.

The invention claimed is:

1. A method for synthesizing dissymmetric sulfoether, comprising:
    a) under the condition of tetrabutylammonium halide catalysis, compounds having a structure of formula (I), compounds having a structure of formula (II) and salts having sulfur and oxygen are reacted in a solvent to give dissymmetric sulfoether having a structure of formula (III);

formula (I)
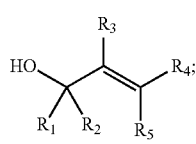

formula (II)
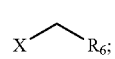

formula (III)
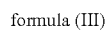

wherein, R1 is selected from phenyl, substituted phenyl, naphthyl, substituted naphthyl, thienyl or substituted thienyl; R2 is selected from hydrogen, phenyl, substituted phenyl, naphthyl, substituted naphthyl, thienyl or substituted thienyl; or R1, R2 form fluorene ring or thioxanthone ring with the C to which it is attached;
R3 is selected from hydrogen or alkyl;
R4 is selected from hydrogen, phenyl, substituted phenyl, naphthyl, substituted naphthyl, thienyl or substituted thienyl; R5 is selected from hydrogen; or R4, R5 form fluorene ring or thioxanthone ring with the C to which it is attached;
R6 is selected from C1~C30 alkyl, cyano-substituted C1~C20 alkyl, cyano-substituted C1~C20 benzyl, C1~C5 alkyl-substituted benzyl, halogen-substituted benzyl, fluorenyl and any of the structural substituents represented in formulas (a-1)~(a-9):

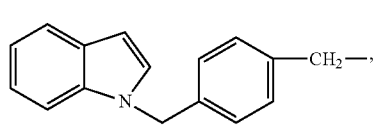
(a-1)

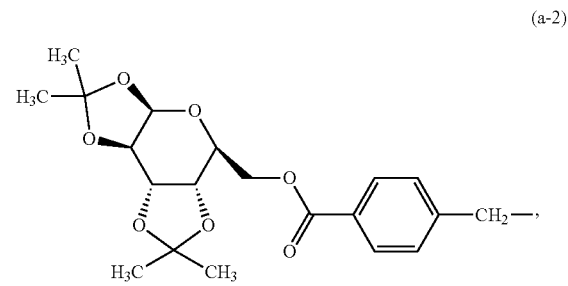
(a-2)

(a-3)
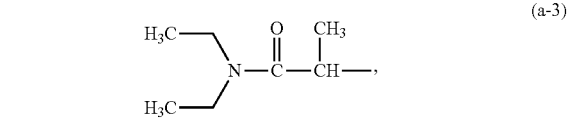

(a-4)
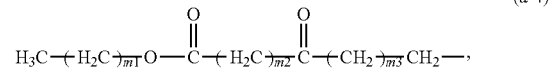

(a-5)
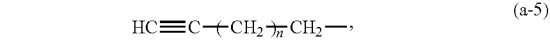

(a-6)

(a-7)
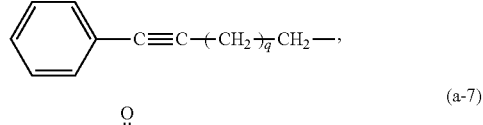

(a-8)
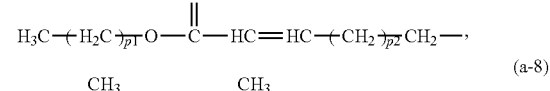

(a-9)
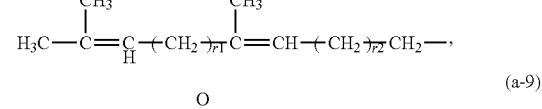

in formulas (a-4)~(a-9), m$_1$, m$_2$, m$_3$, n, q, p$_1$, p$_2$, r$_1$, r$_2$ and e are integer from 0 to 5, respectively;
X is selected from Cl, Br or I;
said salts having sulfur and oxygen include sodium thiosulfate and/or sodium sulfite.

2. The method according to claim 1, wherein,
R1 is selected from phenyl, C1~C5 alkyl-substituted phenyl, C1~C5 alkoxy-substituted phenyl, halogen-substituted phenyl, naphthyl, C1~C5 alkyl-substituted naphthyl, C1~C5 alkoxy-substituted naphthyl, halogen-substituted naphthyl, thienyl, C1~C5 alkyl-substituted thienyl, C1~C5 alkoxy-substituted thienyl or halogen-substituted thienyl;
R2 is selected from hydrogen, phenyl, C1~C5 alkyl-substituted phenyl, C1~C5 alkoxy-substituted phenyl, halogen-substituted phenyl, naphthyl, C1~C5 alkyl-substituted naphthyl, C1~C5 alkoxy-substituted naphthyl, halogen-substituted naphthyl, thienyl, C1~C5 alkyl-substituted thienyl, C1~C5 alkoxy-substituted thienyl or halogen-substituted thienyl;

R3 is selected from hydrogen and C1~C5 alkyl;

R4 is selected from hydrogen, phenyl, C1~C5 alkyl-substituted phenyl, halogen-substituted phenyl, naphthyl, C1~C5 alkyl-substituted naphthyl, halogen-substituted naphthyl, thienyl, C1~C5 alkyl-substituted thienyl or halogen-substituted thienyl.

3. The method according to claim 1, wherein structural compound of formula (I) is 1,1-diphenylpropyl-2-enyl-1-ol, 1,1-bis (4-fluorophenyl) prop-2-enyl-1-ol, 1,1-bis (4-chlorophenyl) prop-2-enyl-1-ol, 1,1-bis (4-bromophenyl) prop-2-enyl-1-ol, 1,1-bis (4-methylphenyl) prop-2-enyl-1-ol, 1,1-bis (4-methoxyphenyl) prop-2-enyl-1-ol, 1-phenyl-1-p-methylphenyl-2-enyl-1-ol, 1-(3,4-dimethylphenyl)-1-phenylprop-2-enyl-1-ol, 1-phenyl-1-p-bromophenyl-2-enyl-1-ol, 1-phenyl-1-o-fluorophenylprop-2-enyl-1-ol, 1-(naphthalen-2-yl)-1-phenylprop-2-enyl-1-ol, 2-methyl-1,1-diphenylprop-2-enyl-1-ol, 9-ethenyl-9H-fluorenyl-9-ol, 9-ethenyl-9H-thioxanthen-9-ol, 1-phenylprop-2-enyl-1-ol, (E)-1,3-diphenylprop-2-enyl-1-ol, (E)-1,3-bis (4-fluorophenyl) prop-2-enyl-1-ol, (E)-1,3-bis (4-chlorophenyl) prop-2-enyl-1-ol, (E)-1,3-bis (4-bromophenyl) prop-2-enyl-1-ol, (E)-1,3-bis (naphthalen-2-yl) prop-2-enyl-1-ol, (E)-1,3-bis (thiophen-2-yl) prop-2-enyl-1-ol or (E)-2-methyl-1,3-diphenylprop-2-enyl-1-ol.

4. The method according to claim 1, wherein structural compound of formula (II) is p-cyanobenzyl chloride, m-cyanobenzyl chloride, p-trifluoromethylbenzyl chloride, o-bromobenzyl chloride, p-methylbenzyl bromide, 9-bromofluorene, (4-(chloromethyl) phenyl) (1H-indol-1-yl) methanone, ((3aR, 5S, 5aS, 8aS, 8bR)-2,2,7,7-tetramethyltetrahydroxy-3aH-bis [1,3] dioxo [4,5-b: 4',5'-d] pyran-5-yl) methyl 4-(chloromethyl) phenyl ester, (3-chloropropyl-1-ynyl) benzene, iodine n-decane, 4-chlorobutyronitrile or ethyl 4-bromobutyrate.

5. The method according to claim 1, wherein said molar ratio of structural compounds of formula (I): structural compounds of formula (II): salts having sulfur and oxygen is 1:(1.5~3):(2~4).

6. The method according to claim 1, wherein temperature of said reaction is 20~90° C.

7. The method according to claim 1, wherein time of said reaction is 3~8 h.

8. The method according to claim 1, wherein in step a), after the completion of reaction having structural compounds of formula (I), structural compounds of formula (II) and salts having sulfur and oxygen, extraction, drying and column chromatography are performed successively to give dissymmetric sulfoether having a structure represented in formula (III).

9. The method according to claim 1, wherein said solvent is water.

* * * * *